(12) United States Patent (10) Patent No.: US 8,715,197 B2
Sawanoi et al. (45) Date of Patent: May 6, 2014

(54) BLOOD PRESSURE INFORMATION MEASUREMENT DEVICE

(75) Inventors: Yukiya Sawanoi, Nara (JP); Kenji Fujii, Kyoto (JP); Naomi Matsumura, Takatsuki (JP); Reiji Fujita, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 434 days.

(21) Appl. No.: 13/033,746

(22) Filed: Feb. 24, 2011

(65) Prior Publication Data

US 2011/0208069 A1 Aug. 25, 2011

Related U.S. Application Data

(63) Continuation of application No. PCT/JP2009/064290, filed on Aug. 13, 2009.

(30) Foreign Application Priority Data

Aug. 29, 2008 (JP) ................................. 2008-221286

(51) Int. Cl.
*A61B 5/02* (2006.01)
(52) U.S. Cl.
USPC .......................................... 600/490; 600/499
(58) Field of Classification Search
USPC ........................... 600/485, 490, 491, 493, 499
See application file for complete search history.

(56) References Cited

U.S. PATENT DOCUMENTS

| 6,802,816 B2 | 10/2004 | Palti et al. |
| 2009/0312652 A1 | 12/2009 | Yamakoshi et al. |

FOREIGN PATENT DOCUMENTS

| JP | 59-156325 | 9/1984 |
| JP | 6-63024 | 3/1994 |
| JP | 2008-36004 A | 2/2008 |
| WO | 2008/015921 A1 | 2/2008 |

OTHER PUBLICATIONS

International Search Report for International Application No. PCT/JP2009/064290, mailed on Sep. 15, 2009 (2 pages).
Patent Abstracts of Japan for Japanese Publication No. 2008-036004, Publication date Feb. 21, 2008 (1 page).
Sawanoi, et al., "A New Method for the Fast Determination of a Servo-Reference Value with Vibration Technique for Monitoring Non-Invasive Instantaneous Blood Pressure Using the Volume-Compensation Technique", Transactions of Japanese Society for Medical, Apr. 10, 2008, vol. 46, No. 2, pp. 218-225 (9 pages).
Patent Abstracts of Japan for Japanese Publication No. 06-063024, Publication date Mar. 8, 1994 (1 page).
Office Action issued in corresponding Chinese Application No. 200980131719.6 dated Nov. 13, 2012, and English translation thereof (7 pages).

*Primary Examiner* — Navin Natnithithadha
*Assistant Examiner* — Etsub Berhanu
(74) *Attorney, Agent, or Firm* — Osha Liang LLP

(57) ABSTRACT

A blood pressure information measurement device instantaneously changes cuff pressure in a specified pressure section in order to detect a control target value in artery volume constant control. An artery volume signal is detected in that period, and an inflection point of the detected artery volume signal is detected by performing differentiation processing or the like. The inflection point of the detected artery volume signal is fixed as the control target value.

10 Claims, 9 Drawing Sheets

| Data | Blood pressure data |
|---|---|
| 1 | BD(1) |
| 2 | BD(2) |
| 3 | BD(3) |
| 4 | — |
| 5 | BD(5) |
| 6 | — |
| 7 | BD(7) |
| 8 | BD(8) |
| 9 | BD(9) |
| ⋮ | ⋮ |
| N | BD(n) |

BLOOD PRESSURE INFORMATION MEASUREMENT DEVICE

TECHNICAL FIELD

The present invention relates to a blood pressure information measurement device, particularly to a blood pressure information measurement device capable of measuring blood pressure information using a volume compensation method.

BACKGROUND ART

Conventionally, blood pressure measurement by the volume compensation method has been developed as a method capable of non-invasively and simply measuring blood pressure. Under the volume compensation method, an artery is compressed by a cuff from the outside of a living body, so that a volume of the artery pulsating in synchronization with a heartbeat is always maintained to be constant. By maintaining the volume of the artery to be constant, pressure (cuff pressure) for compressing a measuring site and internal pressure of the artery of the measuring site, that is, blood pressure, are equilibrated. By detecting the cuff pressure when this equilibrium state is maintained, a blood pressure value is continuously obtained.

Therefore, in the volume compensation method, two points of detection of a volume value when the artery is in an unloaded state, that is, a control target value (hereinafter, also referred to as "V0"), and maintenance of this unloaded state (servo-control) are important. Particularly, decision of V0 is highly important as V0 directly influences precision of blood pressure measurement.

As a decision method of V0, for example, as disclosed in Japanese Unexamined Patent Publication No. 1984-156325 (patent document 1), there is a method of deciding V0 by gradually compressing the artery by a cuff and detecting a maximum point of an artery volume change signal obtained at that time.

Conventionally, there is also a proposal for realizing shortening of a time required for the decision of V0. For example, in Japanese Unexamined Patent Publication No. 2008-36004 (patent document 2), high-frequency small pressure oscillation (such as sine wave pressure oscillation of 20 Hz, 10 mmHg) is superimposed on the cuff pressure, and V0 is decided by detecting a maximum point of an artery volume change due to the high-frequency small pressure oscillation.

It should be noted that with regard to shortening of a time for the blood pressure measurement, the following technology is disclosed in U.S. Pat. No. 6,802,816 (patent document 3) although different from the volume compensation method. That is, the cuff pressure is rapidly increased and reduced within one heartbeat, so that a feature point on a pulse wave indicating an instant when the artery internal pressure is equal to the cuff pressure is detected. The cuff pressure at a time point when the feature point is detected is decided as the blood pressure value.

Patent Document 1: Japanese Unexamined Patent Publication No. 1984-156325
Patent Document 2: Japanese Unexamined Patent Publication No. 2008-36004
Patent Document 3: U.S. Pat. No. 6,802,816

SUMMARY OF INVENTION

In the method of Japanese Unexamined Patent Publication No. 1984-156325, at least 30 seconds are required for the decision of V0. Therefore, a time of not less than 30+α seconds is required from measurement start to first blood pressure decision. During continuous blood pressure measurement, V0 is sometimes changed due to a change in the blood pressure, stress, an environmental change, and the like, so that there is a need for detecting V0 again for each time. In that case, at least 30 seconds are also required for the decision of V0. Therefore, even after starting the continuous blood pressure measurement, the blood pressure cannot be measured during re-decision of V0.

Even when the invention of Japanese Unexamined Patent Publication No. 2008-36004 (patent document 2) is used, there is a need for suppressing pressurization speed of the cuff pressure to about 20 mmHg/sec in order to ensure decision precision of V0. Therefore, about 10 seconds are required for the decision of V0.

Therefore, one or more embodiments of the present invention provides a blood pressure information measurement device of a volume compensation type capable of instantaneously deciding the control target value (V0).

According to one or more embodiments of the present invention, a blood pressure information measurement device for measuring blood pressure information by detecting a volume of an artery includes: a cuff to be wound around a predetermined measuring site; an adjustment unit for adjusting pressure in the cuff by pressurization and depressurization; a pressure detector for detecting cuff pressure representing the pressure in the cuff; a volume detector arranged at a predetermined position of the cuff, the volume detector for detecting an artery volume signal indicating the volume of the artery; and a control unit for performing control for measurement of the blood pressure information by performing servo-control on the adjustment unit so that the volume of the artery is constant, wherein the control unit includes a detection processing unit for detecting a control target value in the servo-control based on the artery volume signal, and the detection processing unit includes: an adjustment control unit for instantaneously changing the cuff pressure in a specified pressure section by controlling the adjustment unit; and a decision unit for detecting an inflection point of the artery volume signal obtained in a control period of the adjustment control unit and deciding the control target value with using the detected inflection point.

According to one or more embodiments of the present invention, the adjustment control unit changes the cuff pressure within one heartbeat of a measuring person.

According to one or more embodiments of the present invention, the decision unit detects the inflection point of the artery volume signal by detecting a maximum point of a differential value of the artery volume signal.

According to one or more embodiments of the present invention, the decision unit decides a value corresponding to the detected inflection point as the control target value.

According to one or more embodiments of the present invention, the adjustment control unit executes change processing of the cuff pressure in the specified pressure section for a predetermined number of times, and the decision unit decides an average value of values corresponding to the inflection point of the artery volume signal obtained in the change processing as the control target value.

According to one or more embodiments of the present invention, the adjustment control unit executes change processing of the cuff pressure in the specified pressure section for a predetermined number of times, and the decision unit decides a representative value of values corresponding to the inflection point of the artery volume signal obtained in the change processing as the control target value.

According to one or more embodiments of the present invention, the specified pressure section is within a range from a predetermined first pressure value to a second pressure value.

According to one or more embodiments of the present invention, the specified pressure section is within a range from a predetermined pressure value to a maximum blood pressure estimate value of a measuring person.

According to one or more embodiments of the present invention, the specified pressure section is within a range from a vicinity of a minimum blood pressure estimate value of a measuring person to a predetermined pressure value.

According to one or more embodiments of the present invention, the specified pressure section is within a range from a vicinity of a minimum blood pressure estimate value of a measuring person to a vicinity of a maximum blood pressure estimate value of the measuring person.

According to one or more embodiments of the present invention, the specified pressure section is within a predetermined pressure range centering around an average blood pressure estimate value of a measuring person.

According to one or more embodiments of the present invention, the cuff pressure is instantaneously changed in the specified pressure section, and the control target value is decided based on the inflection point of the artery volume signal detected in that period. Therefore, the control target value required for continuous blood pressure measurement by the volume compensation method can be decided for a much shorter time than a conventional method.

BRIEF DESCRIPTION OF THE DRAWINGS

FIG. 5(a) shows the conventionally general decision method; and FIG. 5(b) shows the decision method in an embodiment of the present invention.

FIG. 6(a) is a graph showing a relationship between a change in the cuff pressure and virtual artery internal pressure along a time line; and FIG. 6(b) is a graph showing a typical example of a change in the artery volume signal in accordance with the change in the cuff pressure along the same time line as the graph in FIG. 6(a).

DETAILED DESCRIPTION OF THE INVENTION

Figure 1:
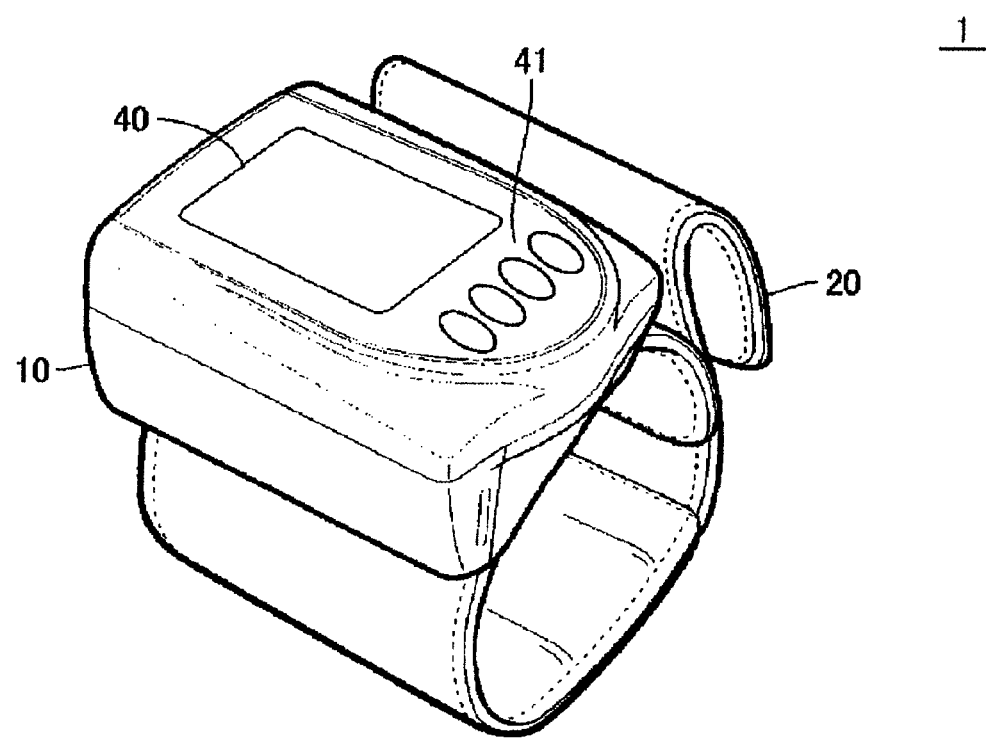
FIG. 1 is a perspective view of an outer appearance of a blood pressure information measurement device according to an embodiment of the present invention.

Embodiments of the present invention will be described in detail with reference to the drawings. It should be noted that the same or corresponding parts in the drawings will be given the same symbols, and description thereof will not be repeated.

A blood pressure information measurement device in an embodiment of the present invention measures blood pressure information based on a volume compensation method. In the present embodiment, the "blood pressure information" is information indicating characteristics of a circulatory system, at least including a pulse wave, and in addition to the pulse wave, further including indicators capable of being calculated from the pulse wave such as a continuous blood pressure value (blood pressure waveform), maximum blood pressure, minimum blood pressure, average blood pressure, the number of pulsations, and an AI (Augmentation Index) value.

The pulse wave serving as one of the blood pressure information includes a pressure pulse wave and a volume pulse wave from a difference in an object to be captured. The pressure pulse wave is determined by converting a variation in an intravascular volume in accordance with pulsation of a heart into a volume change in a cuff and capturing the pulse wave as a variation in the cuff pressure in accordance with a volume change in the cuff, and the pressure pulse wave can be obtained based on an output from a pressure sensor. The volume pulse wave is determined by capturing the pulse wave as the variation in the intravascular volume in accordance with the pulsation of the heart, and the volume pulse wave can be obtained based on an output from an artery volume sensor. It should be noted that the variation in the intravascular volume can be captured as a change in an intravascular blood tissue amount.

The term "blood pressure information measurement device" used in the present specification generally indicates a device at least having a function of acquiring the pulse wave, and more particularly indicates a device for detecting the variation in the blood tissue amount with an optical method and acquiring the volume pulse wave according to the volume compensation method. In this sense, the blood pressure information measurement device is not limited to a device for outputting the acquired volume pulse wave straightaway as a measurement result but includes a device for outputting only the particular indicators as described above, which are calculated or measured based on the acquired volume pulse wave as the measurement result, and a device for outputting both the volume pulse wave and the particular indicators as the measurement results.

(Outer Appearance and Configuration)

(Outer Appearance)

FIG. 1 is a perspective view of an outer appearance of a blood pressure information measurement device 1 according to an embodiment of the present invention. The outer appearance of the blood pressure information measurement device 1 is the same as a general sphygmomanometer.

With reference to FIG. 1, the blood pressure information measurement device 1 is provided with a main body portion 10, and a cuff 20 capable of being wound around a wrist of a measuring person. The main body portion 10 is attached to the cuff 20. A display unit 40 formed by, for example, a liquid crystal or the like, and an operation unit 41 for receiving an instruction from a user (the measuring person) are arranged on a surface of the main body portion 10. The operation unit 41 includes a plurality of switches.

It should be noted that in the present embodiment, the cuff 20 will be described as a part to be attached to the wrist of the measuring person. However, a site (a measuring site) to which the cuff 20 is attached is not limited to the wrist but may be an upper arm, for example.

As shown in FIG. 1, the blood pressure information measurement device 1 in the present embodiment will be described by taking a mode that the main body portion 1 is attached to the cuff 20 as an example. However, the blood pressure information measurement device may be in a mode that the main body portion 10 and the cuff 20 are connected by an air tube (an air tube 31 in FIG. 2) as adopted in a blood pressure information measurement device of an upper arm type.

(Hardware Configuration)

Figure 2:
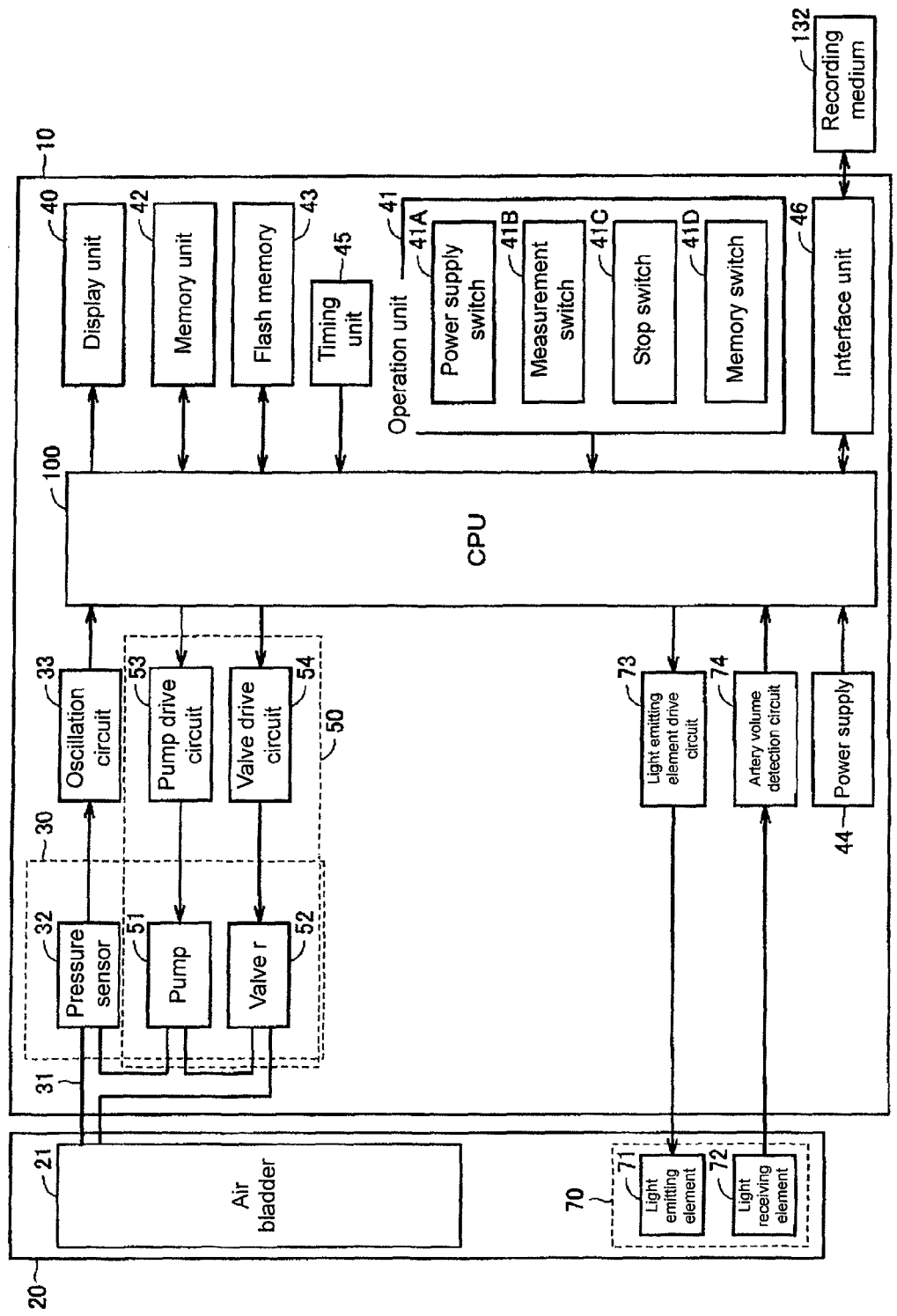
FIG. 2 is a block diagram showing a hardware configuration of the blood pressure information measurement device according to an embodiment of the present invention.

FIG. 2 is a block diagram showing a hardware configuration of the blood pressure information measurement device 1 according to an embodiment of the present invention.

With reference to FIG. 2, the cuff 20 of the blood pressure information measurement device 1 includes an air bladder 21, and an artery volume sensor 70. The artery volume sensor 70 has a light emitting element 71, and a light receiving element 72. The light emitting element 71 applies light to an artery, and the light receiving element 72 receives transmitted light or reflected light of the artery of the light applied by the light emitting element 71. The light emitting element 71 and the light receiving element 72 are arranged, for example, on the inner side of the air bladder 21 so as to be spaced from each other by a predetermined amount.

It should be noted that the artery volume sensor 70 may be any sensor as long as the sensor can detect the volume of the artery, such as an impedance sensor (an impedance plethysmograph) for detecting the volume of the artery. In that case, in place of the light emitting element 71 and the light receiving element 72, a plurality of electrodes (an electrode pair for applying electric currents, and an electrode pair for detecting voltage) for detecting impedance of a site including the artery is included.

The air bladder 21 is connected to an air system 30 via the air tube 31.

In addition to the above display unit 40 and the operation unit 41, the main body portion 10 includes the air system 30, a CPU (Central Processing Unit) 100 for concentrically controlling units and performing various calculation processing, a memory unit 42 for storing a program to have the CPU 100 perform predetermined actions and various data, a nonvolatile memory (such as a flash memory) 43 for storing measured blood pressure information, a power supply 44 for supplying electric power to the CPU 100, a timing unit 45 for performing a timing action, and an interface unit 46 for reading and writing a program and data from and to a detachable recording medium 132.

The operation unit 41 has a power supply switch 41A for receiving an input of an instruction of turning on or off the power supply, a measurement switch 41B for receiving an instruction of measurement start, a stop switch 41C for receiving an instruction of measurement stop, and a memory switch 41D for receiving an instruction of reading information such as the blood pressure recorded in the flash memory 43.

The air system 30 includes a pressure sensor 32 for detecting pressure (cuff pressure) in the air bladder 21, a pump 51 for supplying the air to the air bladder 21 so as to increase the cuff pressure, and a valve 52 opened and closed so as to discharge or enclose the air of the air bladder 21.

The main body portion 10 further includes a light emitting element drive circuit 73, and an artery volume detection circuit 74, and in connection with the air system 30, an oscillation circuit 33, a pump drive circuit 53, and a valve drive circuit 54.

The light emitting element drive circuit 73 has the light emitting element 71 emit the light at a predetermined timing in accordance with a command signal from the CPU 100. The artery volume detection circuit 74 detects an artery volume by converting an output from the light receiving element 72 into a voltage value.

The pressure sensor 32 is, for example, a capacitance pressure sensor in which a volume value is changed by the cuff pressure. The oscillation circuit 33 outputs a signal of an oscillating frequency in accordance with the volume value of the pressure sensor 32 to the CPU 100. The CPU 100 converts the signal obtained from the oscillation circuit 33 into pressure so as to detect the pressure. The pump drive circuit 53 controls drive of the pump 51 based on a control signal given from the CPU 100. The valve drive circuit 54 controls opening/closing of the valve 52 based on a control signal given from the CPU 100.

The pump 51, the valve 52, the pump drive circuit 53, and the valve drive circuit 54 form an adjustment unit 50 for adjusting the pressure in the cuff 20 by pressurization and depressurization. It should be noted that devices forming the adjustment unit 50 are not limited to the above members. For example, the adjustment unit 50 may include an air cylinder and an actuator for driving the air cylinder in addition to the above members.

The air bladder 21 is included in the cuff 20. However, a fluid to be supplied to the cuff 20 is not limited to the air but may be a liquid or gel, for example. Alternatively, embodiments of the present invention are not limited to the fluid but may be uniform and fine particles such as microbeads.

(Functional Configuration)

Figure 3:
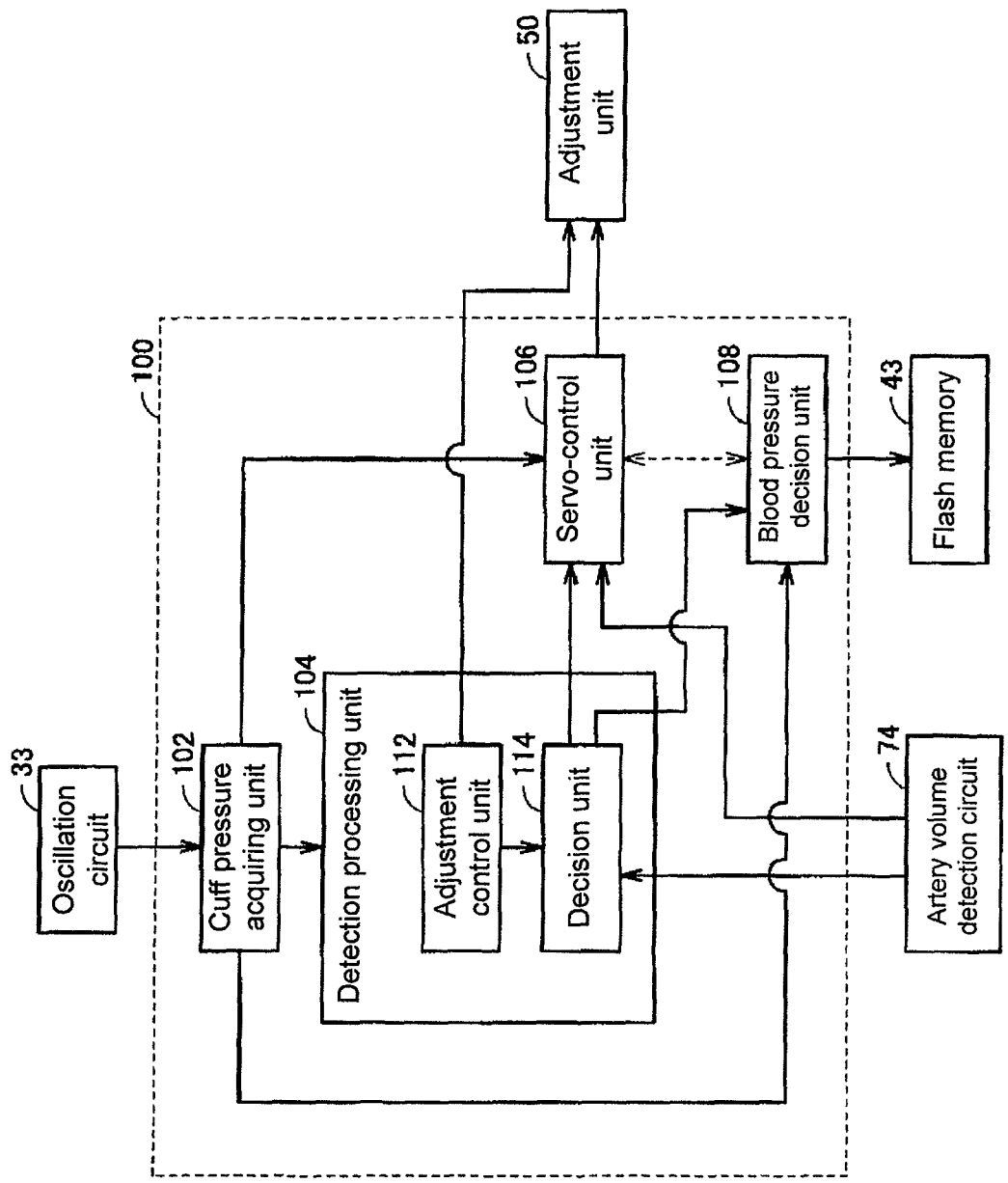
FIG. 3 is a functional block diagram showing a functional configuration of the blood pressure information measurement device according to an embodiment of the present invention.

FIG. 3 is a functional block diagram showing a functional configuration of the blood pressure information measurement device 1 according to an embodiment of the present invention.

With reference to FIG. 3, the CPU 100 includes a cuff pressure acquiring unit 102, a detection processing unit 104, a servo-control unit 106, and a blood pressure decision unit 108. It should be noted that FIG. 3 only shows peripheral hardware, which directly send and receive signals and data to and from these functional blocks for convenience of description.

The cuff pressure acquiring unit 102 acquires the cuff pressure based on the signal from the oscillation circuit 33. More specifically, by converting the signal of the oscillating frequency detected by the oscillation circuit 33 into the pressure, the cuff pressure is acquired. The acquired cuff pressure is outputted to the detection processing unit 104, the servo-control unit 106, and the blood pressure decision unit 108.

The detection processing unit 104 performs detection processing of a control target value V0 and initial control cuff pressure PC0. Specific processing of the detection processing unit 104 in the present embodiment will be described later.

The servo-control unit 106 is connected to the adjustment unit 50, and performs servo-control so that the artery volume corresponds to V0. That is, the servo-control unit performs feedback control on the pressure in the cuff 20 so that a value of an artery volume change signal representing an alternating current component of the artery volume signal becomes "zero".

The blood pressure decision unit 108 continuously decides (measures) the blood pressure in a period of the servo-control. Specifically, the artery volume signal from the artery volume detection circuit 74 and a cuff pressure signal from the cuff pressure acquiring unit 102 are acquired in chronological order, so that the cuff pressure at a time point when a difference between the artery volume value and V0 is not more than a predetermined threshold value is decided as the blood pressure.

It should be noted that in a series of blood pressure measurement periods, the CPU 100 has the light emitting element 71 emit the light at fixed intervals by sending the command signal to the light emitting element drive circuit 73.

Actions of the functional blocks included in the CPU 100 may be realized by executing software stored in the memory unit 42, or at least one of these functional blocks may be realized by hardware.

The specific processing of the detection processing unit 104 will be described.

Firstly, a principle of decision of V0 in the present embodiment will be described using FIGS. 4 to 6.

Figure 4:
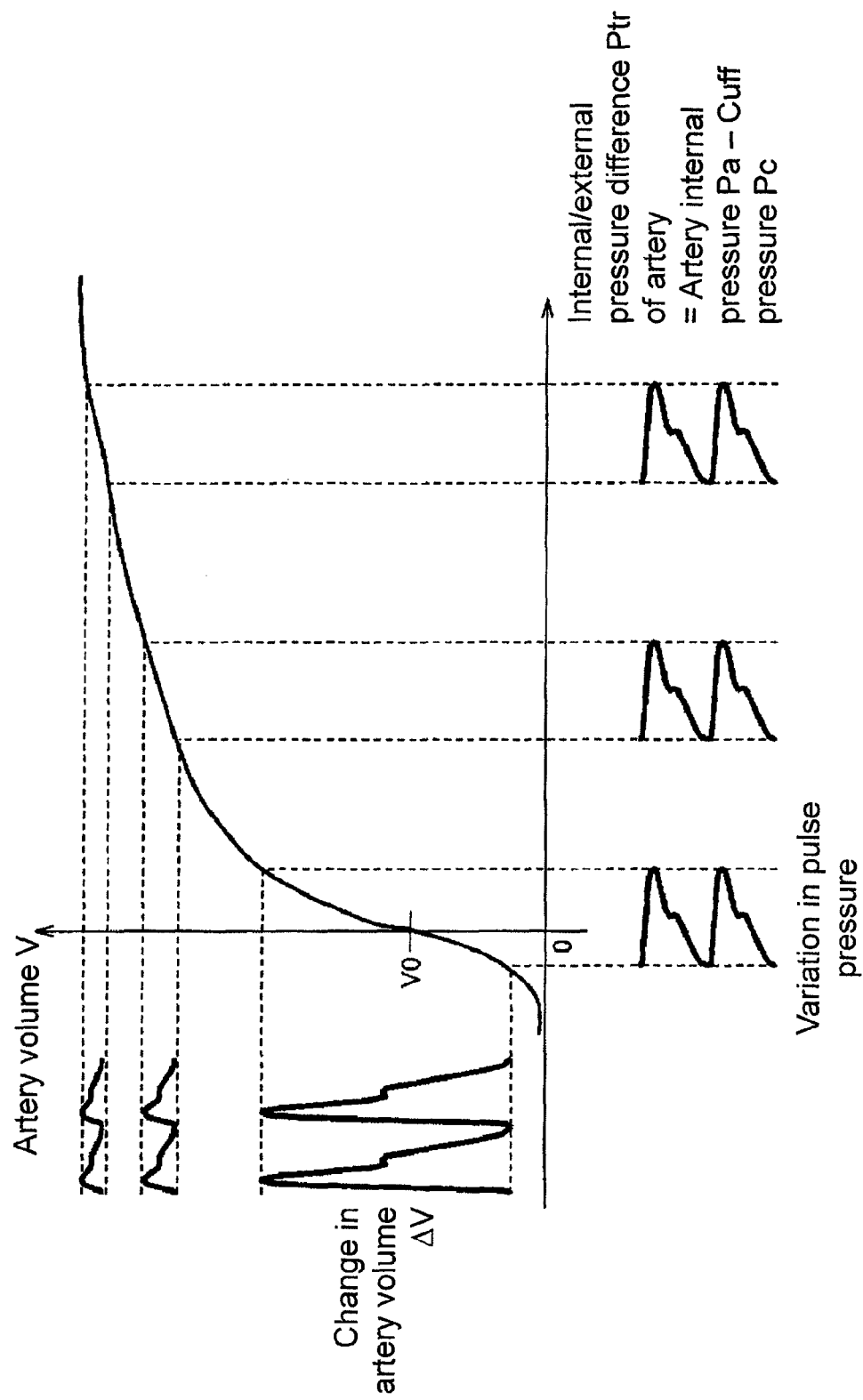
FIG. 4 is a graph showing a mechanical characteristic of an artery.

FIG. 4 is a graph showing a mechanical characteristic of the artery. With the horizontal axis indicating an internal/external pressure difference Ptr, and the vertical axis indicating an artery volume V, the graph of FIG. 4 shows a relationship between the internal/external pressure difference Ptr and the artery volume V. The internal/external pressure difference Ptr shows a difference between an artery internal pressure Pa and a cuff pressure Pc applied by the cuff from the outside of a living body.

As shown in the graph, the mechanical characteristic of the artery generally shows a strong non-linear property. When the internal/external pressure difference Ptr is zero (in an equilibrium state), that is, when an artery wall is in an unloaded state, compliance of the artery (a change amount of the volume due to a pulse beat) is maximum. In other words, a following property (a developing property) of a volume change relative to a pressure change is maximum. In the volume compensation method, by successively controlling the external pressure of the living body (the cuff pressure) so that the detected artery volume is always a volume value at a time point when the internal/external pressure difference Ptr is zero, the blood pressure is measured. Therefore, there is a need for deciding the volume value at the time point when the internal/external pressure difference Ptr is zero, that is, the control target value V0 before the blood pressure measurement.

Figure 5:
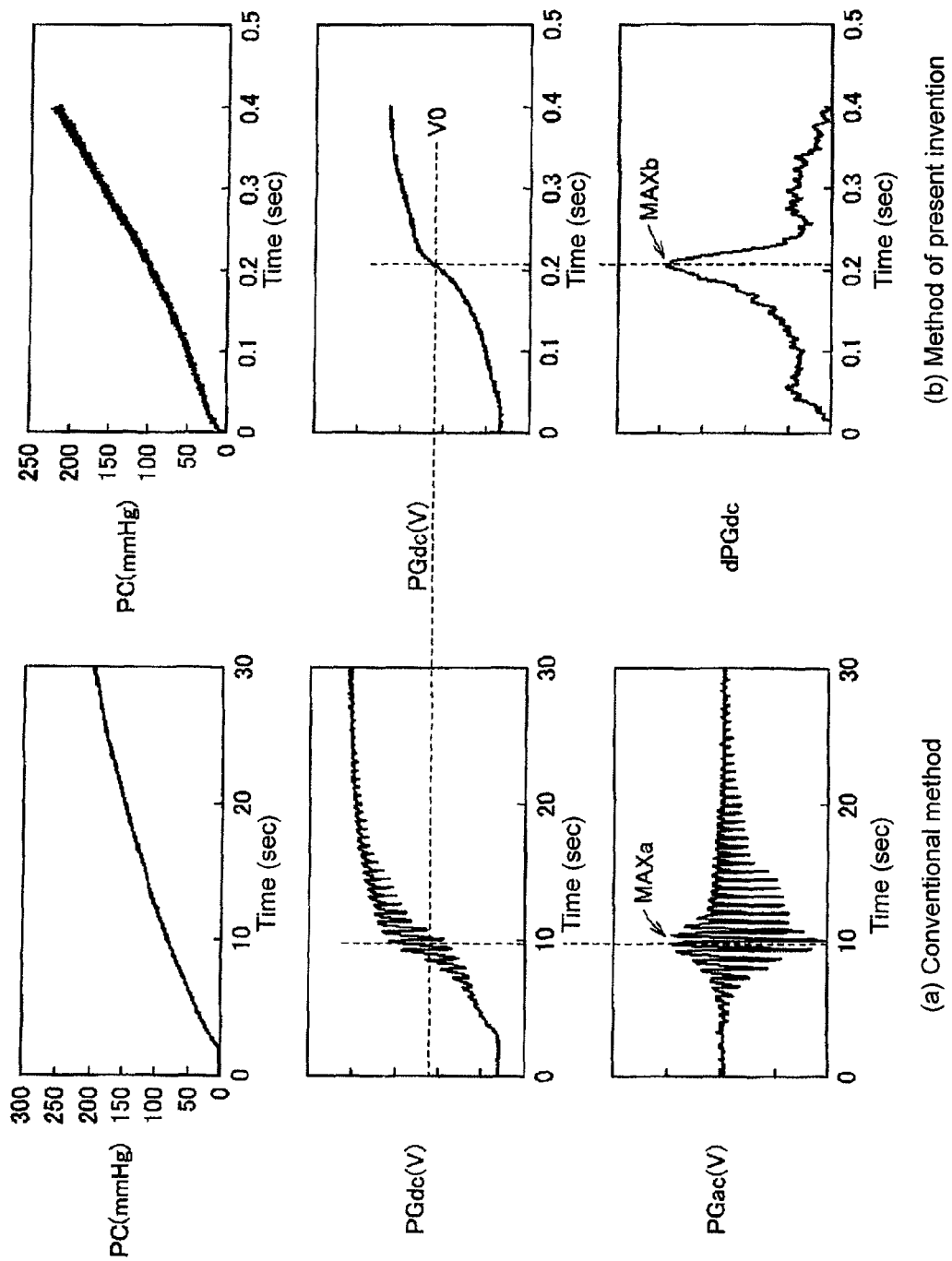
FIG. 5 includes graphs for comparing a conventional control target value decision method and a control target value decision method in an embodiment of the present invention.

FIG. 5 includes graphs for comparing a conventional V0 decision method and a V0 decision method in an embodiment of the present invention. FIG. 5(*a*) shows the conventionally general decision method, and FIG. 5(*b*) shows the decision method according to an embodiment of the present invention.

With reference FIG. 5(*a*), in the conventional method, cuff pressure PC is gradually increased at low speed of about 3 mmHg/sec (a graph on the upper side), and an artery volume signal PGdc is detected in that period (a graph in the middle). A change amount (ΔV) for one beat of the artery volume signal PGdc, that is, an artery volume change signal PGac is detected, and a point MAXa where the artery volume change signal PGac is maximum is detected (a graph on the lower side). An average value of the artery value signal PGac at a time point when the maximum point MAXa is detected is decided as V0. Therefore, in the conventional method, not less than 30 seconds are generally required for decision of V0.

Meanwhile, in the embodiment of the present invention, by focusing on the fact that a point of V0 is a point where the compliance of the artery is maximum, that is, a point where the cuff pressure and the artery internal pressure are equilibrated, the maximum point of the compliance of the artery is detected by the artery volume signal during the change in the cuff pressure (during the pressurization or the depressurization), so that V0 is decided at high speed.

Figure 6:
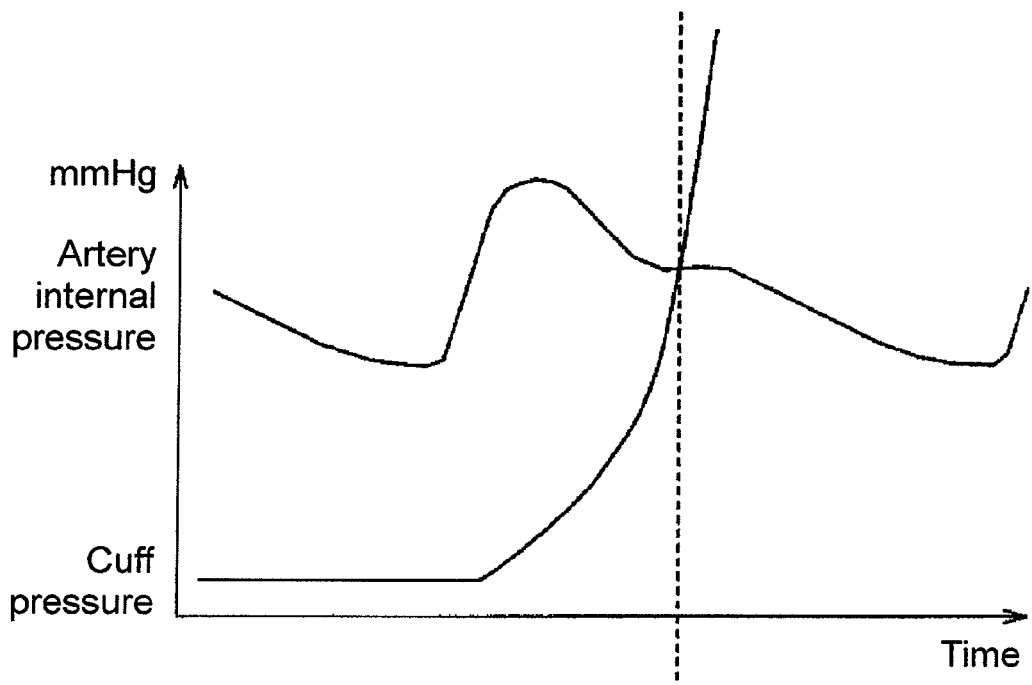
FIG. 6 includes graphs showing a characteristic of an artery volume signal in a case where cuff pressure is instantaneously increased.
Figure 6:
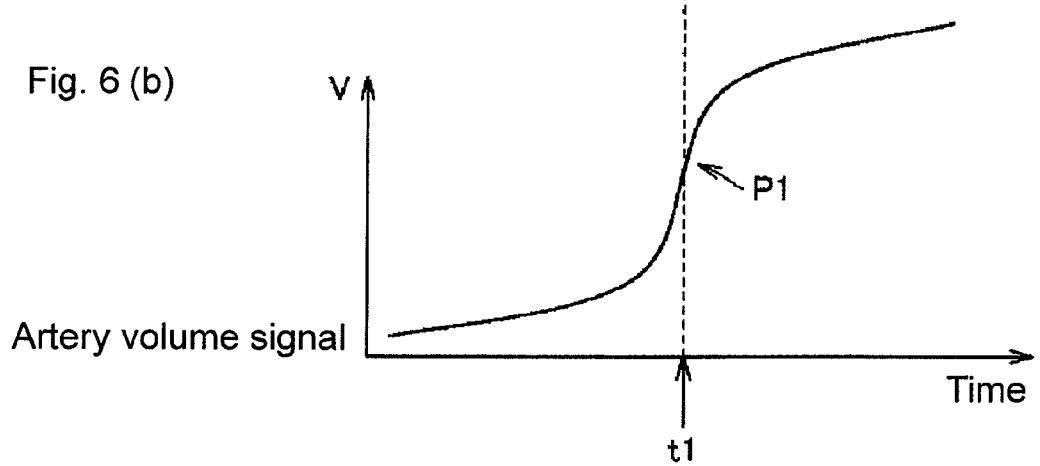

FIG. 6 includes graphs showing a characteristic of the artery volume signal in a case where the cuff pressure is instantaneously increased. FIG. 6(*a*) shows a relationship between the change in the cuff pressure and virtual artery internal pressure along a time line. FIG. 6(*b*) shows a typical example of a change in the artery volume signal in accordance with the change in the cuff pressure along the same time line as FIG. 6(*a*).

As described above, U.S. Pat. No. 6,802,816 (patent document 3) discloses a technology of rapidly increasing and reducing the cuff pressure within one heartbeat, so that a feature point (an inflection point) on the pulse wave indicating an instant when the artery internal pressure is equal to the cuff pressure is detected, and the cuff pressure at that time point is decided as the blood pressure value.

With reference to FIGS. 6(*a*) and 6(*b*), when the cuff pressure is instantaneously increased, a point P1 of the artery volume signal PGdc at a time point t1 when the cuff pressure and the artery internal pressure correspond to each other is the maximum point of the compliance of the artery. Therefore, the inflection point is generated in the artery volume signal PGdc at the point P1. When the inflection point of the artery volume signal PGdc is detected according to this principle, a value of the artery volume signal PGdc at that time can be decided as V0. The inflection point can be easily detected by a method of differentiating the artery volume signal PGdc or the like.

As described above, with reference to FIG. 3 again, the detection processing unit 104 in the present embodiment has an adjustment control unit 112 for instantaneously changing the cuff pressure in a specified pressure section, and a decision unit 114 for deciding the inflection point of the artery volume signal obtained in a control period of the adjustment control unit 112 as the control target value. It should be noted that the phrase "changing the cuff pressure" indicates either increasing the cuff pressure or reducing the cuff pressure, and the former is applied to the present embodiment.

Specifically, with reference to FIG. 5(*b*), the adjustment control unit 112 instantaneously (within one heartbeat) increases the cuff pressure by controlling the pump drive circuit 53 and the valve drive circuit 54 of the adjustment unit 50 (a graph on the upper side). The decision unit 114 detects the artery volume signal PGdc from the artery volume detection circuit 74 in that period (a graph in the middle). In order to detect the inflection point of the artery volume signal PGdc, for example, a maximum point MAXb of a differential value dPGdc of the artery volume signal is detected (a graph on the lower side). The decision unit 114 decides a value of the artery volume signal PGdc at a time point when the maximum point MAXb is detected as V0. The decision unit 114 also decides the cuff pressure at the time point when the maximum point MAXb is detected as the control initial cuff pressure (hereinafter, also called as "PC0").

The servo-control unit 106 performs the servo-control so that V0 decided in such a way corresponds to the artery volume.

(Action)

Figure 7:
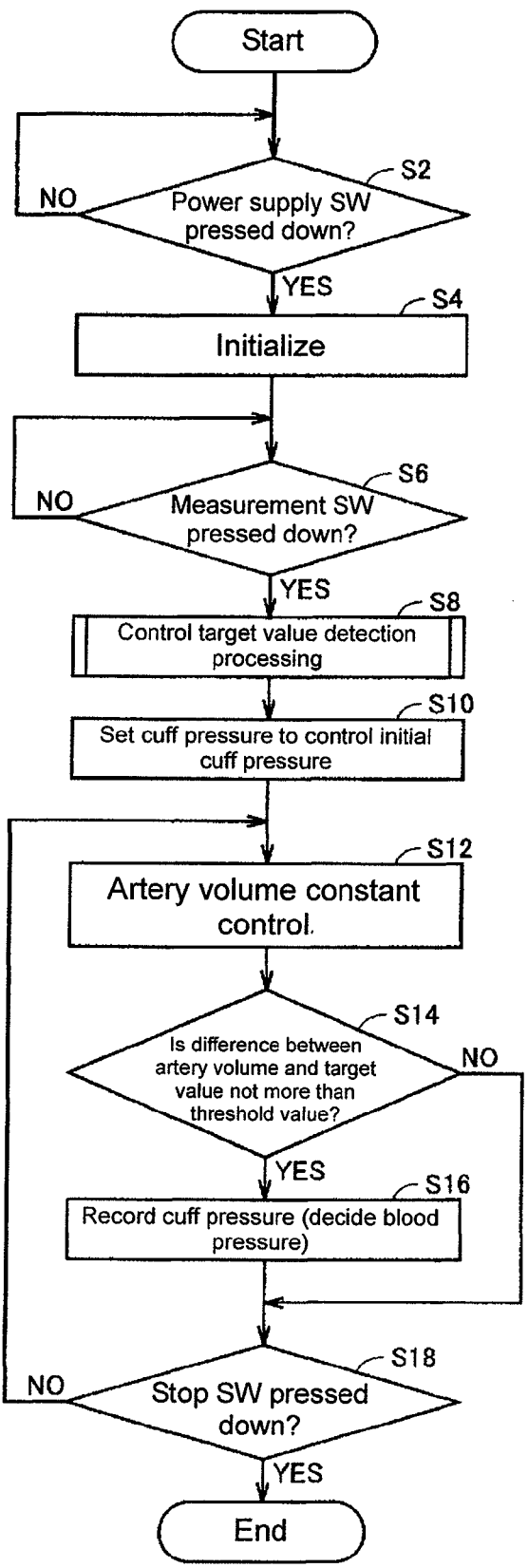
FIG. 7 is a flowchart showing blood pressure measurement processing in an embodiment of the present invention.

FIG. 7 is a flowchart showing blood pressure measurement processing in an embodiment of the present invention. The processing shown in the flowchart of FIG. 7 is preliminarily stored in the memory unit 42 as a program. The CPU 100 reads out and executes this program, so that functions of the blood pressure measurement processing are realized.

With reference to FIG. 7, the CPU 100 determines whether or not the power supply switch 41A is pressed down (Step S2). In a case where the CPU determines that the power supply switch 41A is pressed down (YES in Step S2), the flow proceeds to Step S4.

In Step S4, the CPU 100 performs initialization processing. Specifically, a predetermined area of the memory unit 42 is initialized, the air of the air bladder 21 is exhausted, and the pressure sensor 32 is corrected to 0 mmHg.

When the initialization is finished, the CPU 100 determines whether or not the measurement switch 41B is pressed down (Step S6), and stands by until the measurement switch 41B is pressed down. When the CPU determines that the measurement switch 41B is pressed down (YES in Step S6), the flow proceeds to Step S8.

In Step S8, the detection processing unit 104 executes control target value detection processing. That is, V0 and PC0 are decided. The control target value detection processing will be described with using a flowchart of FIG. 8.

Figure 8:
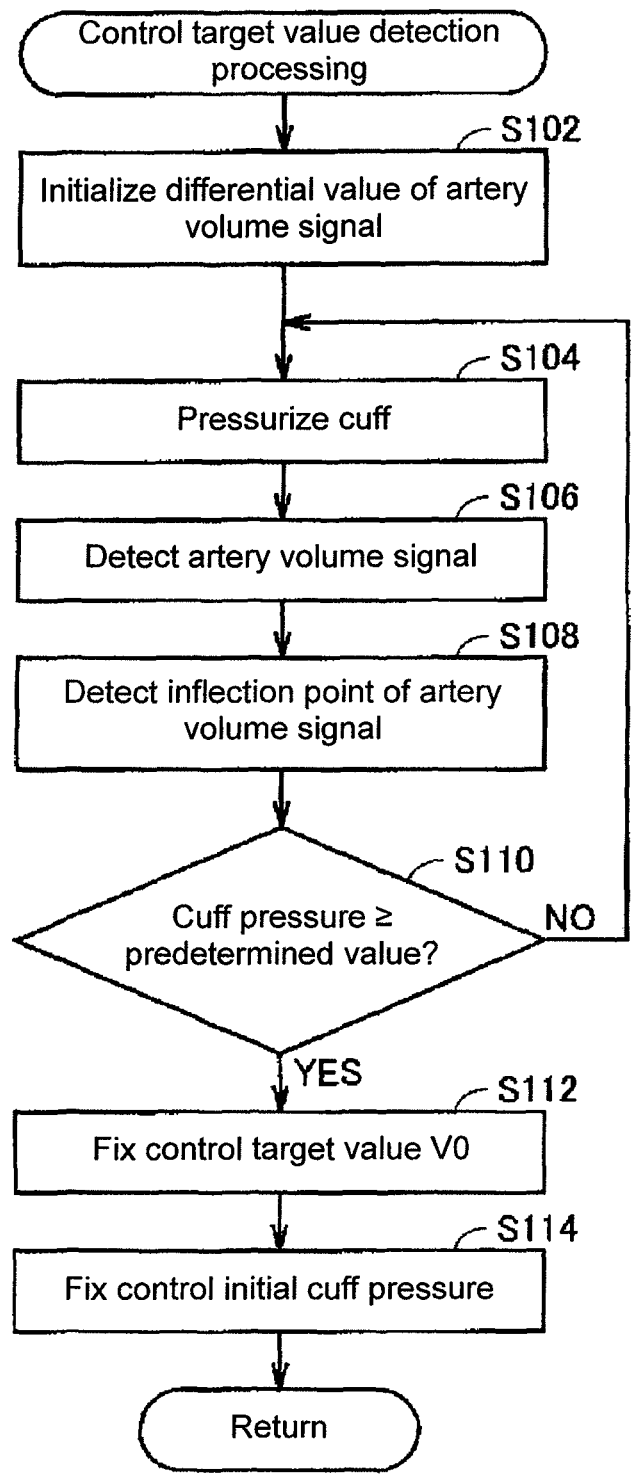
FIG. 8 is a flowchart showing control target value detection processing in an embodiment of the present invention.

FIG. 8 is the flowchart showing the control target value detection processing in an embodiment of the present invention.

With reference to FIG. 8, firstly, the decision unit 114 of the detection processing unit 104 initializes a differential value memory area (such as a predetermined area of the memory unit 42) for storing the maximum value of the differential value of the artery volume signal (Step S102).

Next, the adjustment control unit 112 of the detection processing unit 104 starts the pressurization of the cuff 20 by sending a control signal to the adjustment unit 50 (Step S104). Speed of the pressurization is anything or a predetermined speed as long as the cuff pressure in the specified pressure section can be increased within one heartbeat of the measuring person. The predetermined speed is preferably speed in consideration with pulse pressure and a heart rate of a general adult. Specifically, the predetermined speed may be set, for example, between 0.3 to 0.8 mmHg/ms, or more preferably between 0.4 to 0.6 mmHg/ms.

A lower limit (a minimum value) and an upper limit (a maximum value) in the specified section are respectively predetermined values (such as the lower limit of 0 mmHg and the upper limit of 280 mmHg) in the present embodiment. However, both the lower limit and the upper limit are not limited to the predetermined values. Since the cuff pressure of which V0 is detected is in the vicinity of average blood pressure, the lower limit may be in the vicinity of a lowest blood pressure estimate value of the measuring person, and the upper limit may be in the vicinity of a highest blood pressure estimate value of the measuring person. The vicinity of the lowest blood pressure estimate value is, for example, any value within a range of the lowest blood pressure estimate value±predetermined pressure (such as 10 mmHg). A relative value (including "zero") serving as a lower limit value within the range relative to the lowest blood pressure estimate value is preliminarily fixed. The vicinity of the highest blood pressure estimate value is, for example, any value within a range of the highest blood pressure estimate value±predetermined pressure (such as 10 mmHg). A relative value serving as an upper limit value within the range relative to the highest blood pressure estimate value is preliminarily fixed.

Alternatively, the specified pressure section may be a predetermined pressure range centering around an average blood pressure estimate value of the measuring person. The predetermined pressure range is, for example, a range from "(average blood pressure estimate value)−(predetermined pressure (such as 20 mmHg))" to "(average blood pressure estimate value)+(predetermined pressure (such as 20 mmHg))".

It should be noted that the above upper limit and the lower limit may be interchanged and combined. The above blood pressure estimate values may be values based on the past measurement results (such as the previous measurement results) stored in the flash memory 43, or may be values inputted from the outside. The latter values include, for example, values inputted via the operation unit 41, values inputted from the interface unit 46, and the like.

When the pressurization of the cuff 20 is started, the decision unit 114 of the detection processing unit 104 detects the artery volume signal from the artery volume detection circuit 74 (Step S106). At the same time, the cuff pressure is inputted from the cuff pressure acquiring unit 102. The value of the detected artery volume signal is temporarily stored in chronological order relating to the cuff pressure.

The decision unit 114 detects whether or not the inflection point of the artery volume signal exists (Step S108). Specifically, as described above, the differential value of the artery volume signal detected in Step S106 is firstly calculated. The decision unit determines whether or not the differential value is maximum. More specifically, the decision unit 114 updates the differential value memory area until the calculated differential value becomes less than a differential value recorded in the differential value memory area (hereinafter, referred to as the "provisional maximum differential value"). In a case where the calculated differential value becomes less than the provisional maximum differential value, the decision unit determines that the provisional maximum differential value is a final maximum value. The decision unit determines a point of the artery volume signal at a time point when the maximum value is detected as the inflection point of the artery volume signal.

Until the internal pressure of the cuff 20 reaches a predetermined value (such as 280 mmHg) (NO in Step S110), the processing of Steps S104 to S108 are repeated. It should be noted that the processing of Steps S104 to S108 may be executed in parallel.

When the cuff pressure reaches the predetermined value (YES in Step S104), the decision unit 114 fixes the value of the artery volume signal matching with the inflection point of the artery volume signal as V0 (Step S112). The detection processing unit 104 fixes the cuff pressure at the time point when the inflection point is detected as PC0 (Step S114). When this processing is finished, the flow is returned to a main routine.

With reference to FIG. 7 again, when V0 and PC0 are decided, the servo-control unit 106 sets the cuff pressure as PC0 (Step S10).

Next, the servo-control unit 106 executes artery volume constant control so that the artery volume signal corresponds to V0 (Step S12). That is, by controlling the adjustment unit 50, the feedback control is performed on the cuff pressure so that the value of the artery volume change signal is substantially zero. The artery volume change signal can be obtained, for example, by performing filter processing on the artery volume signal.

In parallel to such artery volume constant control, the blood pressure decision unit 108 determines whether or not the difference between the artery volume (the value indicated by the artery volume signal) and V0 is not more than the predetermined threshold value (Step S14). That is, the blood pressure decision unit determines whether or not the value of the volume change signal is close to zero (not more than the predetermined threshold value).

In a case where the blood pressure decision unit determines that the difference between the artery volume and V0 is not more than the threshold value (YES in Step S14), the blood pressure decision unit 108 determines the cuff pressure at that time as the blood pressure and stores the cuff pressure in the flash memory 43 (Step S16). When the processing of Step S16 is finished, the flow proceeds to Step S18.

Meanwhile, in a case where the blood pressure decision unit determines that the difference between the artery volume and V0 exceeds the predetermined threshold value (NO in Step S14), the flow proceeds to Step S18. That is, when it cannot be said that the artery volume and V0 substantially correspond to each other, the cuff pressure at that time is not decided as the blood pressure value.

In Step S18, the servo-control unit 106 determines whether or not the stop switch 41C is pressed down. In a case where the servo-control unit determines that the stop switch 41C is not pressed down (NO in Step S18), the flow is returned to Step S12. In a case where the servo-control unit determines that the stop switch 41C is pressed down (YES in Step S18), a series of the blood pressure measurement processing is finished. It should be noted that in the present embodiment, in a case where the press-down of the stop switch 41C is detected, the blood pressure measurement processing is finished. However, the blood pressure measurement processing may be finished in a case where a predetermined time elapses after the artery volume constant control is started.

As described above, in the present embodiment, V0 is decided by utilizing the inflection point of the artery volume signal obtained by increasing the cuff pressure rapidly (for example, at speed of 0.5 mmHg/ms). Thus, V0 is detected for only about 0.4 seconds. Since there is no need for gradually changing the cuff pressure for the decision of V0 unlike the conventional method, V0 can be decided for much shorter time than the conventional method. As a result, a restraint time of the measuring person can be shortened more than the conventional method.

It should be noted that although the present method is adopted in the first decision of V0 in the present embodiment, the method may be adopted when V0 is re-decided for responding to a variation in the blood pressure, a variation in the artery volume, body movement in a period of continuous blood pressure measurement.

In the present embodiment, the cuff pressure is increased to a predetermined value, so that V0 is detected. However, the pressurization may be stopped at the time point when the inflection point of the artery volume signal is detected. Thereby, the time required for the decision of V0 can be further shortened.

V0 is not necessarily detected at the time of the pressurization, but the cuff pressure may be preliminarily set to be high, so that V0 is detected at the time of the depressurization.

In order to increase decision precision of V0, the cuff pressure may be repeatedly increased, decreased, or increased and decreased for several times (the predetermined number of times), so that the inflection points are detected for several times. In that case, an average value or a representative value of a plurality of volume values (corresponding to V0 in the above embodiment, hereinafter called as the "inflection volume values") respectively corresponding to a plurality of the inflection points may be V0. The representative value is, for example, an average value of the inflection volume values excluding a maximum value and a minimum value of the inflection volume values detected for the several times. In such a way, even in a case where the inflection points are detected for several times, one inflection volume value is decided for only about 0.4 seconds. Thus, V0 can be detected for a shorter time than the conventional method and more precisely than a case where V0 is detected at once.

It should be noted that in the present embodiment, the blood pressure information measurement device 1 measures a blood pressure waveform by continuously measuring the blood pressure, and records blood pressure waveform data in the flash memory 43. However, embodiments of the present invention are not limited to such a mode. For example, the continuously obtained blood pressure may be temporarily recorded in the memory unit 42, and the other blood pressure information may be recorded in the flash memory 43. The other blood pressure information may include maximum blood pressure and minimum blood pressure for one beat. Alternatively, the other blood pressure information may include AI (Augmentation Index) capable of being calculated by applying predetermined algorithm to the blood pressure waveform based on the continuously obtained blood pressure.

Alternatively, the continuously obtained blood pressure may be temporarily recorded in the memory unit 42, and the blood pressure waveform may be displayed on the display unit 40 in real-time.

(Data Structure)

Next, data structure examples of measurement data stored in the flash memory 43 by the blood pressure measurement processing in the above embodiment will be described.

Figure 9:
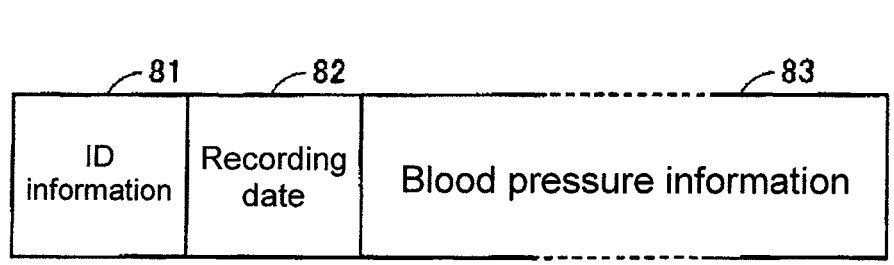
FIG. 9(a) is a diagram showing a data structure of measurement data in an embodiment of the present invention.
FIG. 9(b) is a diagram showing a data structure of a blood pressure information field included in measurement data in an embodiment of the present invention.

FIG. 9(a) is a diagram showing a data structure of the measurement data in the blood pressure information measurement device 1 in an embodiment of the present invention.

With reference to FIG. 9(a), measurement data 80 stored in the flash memory 43 includes three fields 81 to 83 of "ID information", "recording date", and "blood pressure information" as one example. Contents of the fields will be briefly described. The "ID information" field 81 stores identification numbers for specifying the measurement data, and the "recording date" field 82 stores information timed by the timing unit 45 such as a measurement start date and a measurement period of the measurement data. The "blood pressure information" field 83 stores the blood pressure data in chronological order, that is, the blood pressure waveform data.

FIG. 9(b) is a diagram showing a data structure of the blood pressure information field 83 included in the measurement data. With reference to FIG. 9(b), the blood pressure information field 83 has an area 831 for storing "time data", and an area 832 for storing "blood pressure data".

The area 831 stores a plurality of time data 1, 2, 3, . . . , N in accordance with a sampling cycle. The area 832 stores blood pressure data BD(1), BD(2), . . . , BD(n) respectively relating to the time data of the area 831. An area shown by "–" in the area 832 indicates that the difference between the value of the artery volume and the control target value at that time point exceeds the predetermined value and is not recorded as the blood pressure.

It should be noted that a storage mode is not limited to such an example as long as the time and the blood pressure are stored relating to each other.

In such a way, the blood pressure information is stored in the flash memory 43. The blood pressure information may include the indicators capable of being calculated from the blood pressure waveform such as the number of the pulsations and the AI in addition to the blood pressure value such as the maximum blood pressure, the minimum blood pressure, and the average blood pressure.

As described above, the embodiments disclosed herein are illustrative in all aspects and should not be construed as being restrictive. The technical scope of the present invention is defined by the claims, and meanings equivalent to the claims and all modifications within the scope are intended to be encompassed herein.

DESCRIPTION OF SYMBOLS

1: Blood pressure information measurement device
10: Main body portion

20: Cuff
21: Air bladder
30: Air system
31: Air tube
32: Pressure sensor
33: Oscillation circuit
40: Display unit
41: Operation unit
41A: Power supply switch
41B: Measurement switch
41C: Stop switch
41D: Memory switch
42: Memory unit
43: Flash memory
44: Power supply
45: Timing unit
46: Interface unit
50: Adjustment unit
51: Pump
52: Valve
53: Pump drive circuit
54: Valve drive circuit
70: Artery volume sensor
71: Light emitting element
72: Light receiving element
73: Light emitting element drive circuit
74: Artery volume detection circuit
100: CPU
102: Cuff pressure acquiring unit
104: Detection processing unit
106: Servo-control unit
108: Blood pressure decision unit
112: Adjustment control unit
114: Decision unit
132: Recording medium

The invention claimed is:

1. A blood pressure information measurement device for measuring blood pressure information by detecting a volume of an artery, comprising:
   a cuff to be wound around a predetermined measuring site;
   an adjustment unit that adjusts pressure in the cuff by pressurization and depressurization;
   a pressure detector that detects cuff pressure representing the pressure in the cuff;
   a volume detector arranged at a predetermined position of the cuff, wherein the volume detector detects an artery volume signal indicating the volume of the artery; and
   a control unit that controls measurement of the blood pressure information by performing servo-control on the adjustment unit so that the volume of the artery is constant,
   wherein the control unit includes a detection processing unit that detects a control target value in the servo-control based on the artery volume signal, and
   wherein the detection processing unit comprises:
      an adjustment control unit that instantaneously changes the cuff pressure in a specified pressure range by controlling the adjustment unit; and
      a decision unit that detects an inflection point of the artery volume signal obtained in a control period of the adjustment control unit and decides the control target value with using the detected inflection point,
      wherein the decision unit comprises a differentiation unit that differentiates the artery volume signal, so that when the differentiation unit produces a maximum differential value, the inflection point is detected.

2. The blood pressure information measurement device according to claim 1, wherein the control period of the adjustment control unit is within one heartbeat of a measuring person.

3. The blood pressure information measurement device according to claim 1, wherein the decision unit decides a value corresponding to the detected inflection point as the control target value.

4. The blood pressure information measurement device according to claim 1, wherein
   the adjustment control unit executes change processing of the cuff pressure in the specified pressure range for a predetermined number of times, and
   the decision unit decides an average value of values corresponding to the inflection point of the artery volume signal obtained in the change processing as the control target value.

5. The blood pressure information measurement device according to claim 1, wherein
   the adjustment control unit executes change processing of the cuff pressure in the specified pressure range for a predetermined number of times, and
   the decision unit decides a representative value of values corresponding to the inflection point of the artery volume signal obtained in the change processing as the control target value.

6. The blood pressure information measurement device according to claim 1, wherein the specified pressure range is within a range from a predetermined first pressure value to a second pressure value.

7. The blood pressure information measurement device according to claim 1, wherein the specified pressure range is within a range from a predetermined pressure value to a maximum blood pressure estimate value of a measuring person.

8. The blood pressure information measurement device according to claim 1, wherein the specified pressure range is within a range from a vicinity of a minimum blood pressure estimate value of a measuring person to a predetermined pressure value.

9. The blood pressure information measurement device according to claim 1, wherein the specified pressure range is within a range from a vicinity of a minimum blood pressure estimate value of a measuring person to a vicinity of a maximum blood pressure estimate value of the measuring person.

10. The blood pressure information measurement device according to claim 1, wherein the specified pressure range is within a predetermined pressure range centering around an average blood pressure estimate value of a measuring person.

* * * * *